United States Patent [19]

Badziong et al.

[11] Patent Number: 5,095,092
[45] Date of Patent: Mar. 10, 1992

[54] PROCESS FOR THE ISOLATION AND PURIFICATION OF HIRUDIN

[75] Inventors: Werner Badziong, Bad Soden am Taunus; Peter Crause, Offenbach; Paul Habermann; Dominique Tripier, both of Eppstein/Taunus, all of Fed. Rep. of Germany

[73] Assignee: Hoechst Aktiengesellschaft, Frankfurt am Main, Fed. Rep. of Germany

[21] Appl. No.: 590,581

[22] Filed: Sep. 27, 1990

Related U.S. Application Data

[63] Continuation of Ser. No. 269,338, Nov. 10, 1988, abandoned.

[30] Foreign Application Priority Data

Nov. 13, 1987 [DE] Fed. Rep. of Germany ....... 3738541

[51] Int. Cl.$^5$ .......................... C07K 1/14; C07K 3/18; C07K 15/08
[52] U.S. Cl. .................................. 530/324; 530/305; 530/415; 530/417; 530/427
[58] Field of Search ............... 530/305, 324, 412, 415, 530/417, 427

[56] References Cited

U.S. PATENT DOCUMENTS

| | | |
|---|---|---|
| 4,451,455 | 5/1984 | Vertsey et al. |
| 4,616,078 | 10/1986 | DiMarchi ............................. 530/305 |
| 4,617,376 | 10/1986 | Markalioh et al. .................. 530/308 |
| 4,668,662 | 5/1987 | Tripier . |
| 4,791,100 | 12/1988 | Kramer et al. |
| 4,801,576 | 1/1989 | Fritz et al. |

FOREIGN PATENT DOCUMENTS

| | | |
|---|---|---|
| 85/43655 | 12/1985 | Australia . |
| 0158986 | 10/1985 | European Pat. Off. |
| 0209061 | 1/1986 | European Pat. Off. |
| 0197764 | 10/1986 | European Pat. Off. |
| 0200655 | 11/1986 | European Pat. Off. |
| 3526995 | 2/1987 | Fed. Rep. of Germany . |

OTHER PUBLICATIONS

McCormick, D. 1987, Bio/Technology 5:246–250.
Ochoa, J. 1978, Biochimii 60:1–15.
Strop et al., 1978, J. Chromatog, 156:239–254.
Strop, P. 1984, J. Chromatog. 294:213–221.
Miker et al. 1978, J. Chromatog. 153:23–36.
Scoper, R. K. 1987 Protein Purification, Springer Verlag, N.Y. pp. 45–54, 93–99 and 176–179.
Markwardt, F. 1985 Biomed. Biochim. Acta 44(7/8):1007–1013.
Pharmacia 1986, Separation News 13.6:1–6 Bulletin No. 50-01-339.
Dodt, J. et al., 1985 Biol. Chem. Hoppe-Seyler 366:379–385.
Lehninger, A. L. 1975 Biochemistry, Worth Publishers, Inc., NY, NY, pp. 818–819.
Clore et al., "The Conformations of Hirudin in Solution: A Study Using Nuclear Magnetic Resonance, Distance Geometry and Restrained Molecular: Dynamics" The EMBO Journal, vol. 6, No. 2, pp. 529–537, 1987.
Singleton et al., "Dictionary of Microbiology" A Wiley–Interscience Publication.
New Matrex Cellufine Media, Technical Data, AMICON.
HP High Porous Polymer, Data Sheet, Diaion.
XAD Adsorbent Resins, Sales Catalogue, AMBERLITE.
F. Markwardt, Biomed. Biochem. Acta 44 (1985), pp. 1007–1013.
P. Walsmann and F. Markwardt, Thromb. Research, vol. 40 (1985), pp. 563–570.

Primary Examiner—Robert A. Wax
Assistant Examiner—Keith C. Furman
Attorney, Agent, or Firm—Finnegan, Henderson, Farabow, Garrett, and Dunner

[57] ABSTRACT

The invention relates to a process for the isolation and purification of hirudin from complex and salt-containing solutions by hydrophobic chromatography, using as stationary phase porous adsorber resins and as mobile phase organic solvents which are miscible with water.

6 Claims, No Drawings

PROCESS FOR THE ISOLATION AND PURIFICATION OF HIRUDIN

This application is a continuation of application Ser. No. 07/269,338, filed Nov. 10, 1988, now abandoned.

DESCRIPTION

The invention relates to a process for the isolation and purification of hirudin from complex culture filtrates and salt-containing solutions. The polypeptide hirudin, which was originally isolated from the leech Hirudo medicinalis, is a highly specific thrombin inhibitor with a broad therapeutic potential (F. Markwardt, Biomed. Biochim. Acta 44 (1985) 1007-1013). However, the amounts required can be prepared only by means of gene manipulation via transformed microorganisms. It has emerged from this that the yeast Saccharomyces cerevisiae is suitable as a host organism for producing correctly folded and fully active hirudin (EP A1 168 342, EP A1 200 655). The secretion of the protein yields concentrations of up to a few hundred milligrams of hirudin per liter of culture filtrate. However, a high yield of the protein can be achieved only when the nutrient media used for the yeast fermentation are complex, with the addition of yeast extract, cornsteep, peptone or meat paste, so that the problem which arises in the purification of the protein is to isolate hirudin from high dilution in a mixture of concomitant protein-like materials. Ion exchange chromatography, as has been described for the isolation of hirudin from leech extracts (P. Walsmann and F. Markwardt, Thromb. Res. 40 (1985) 563-570), is unsuitable as the first step because of the high salt content of the nutrient solutions used. The process of ultrafiltration which is commonly employed for removing salts from and for concentrating the protein solution also has considerable disadvantages. Thus, costly equipment has to be installed, mass production is limited owing to the long duration of the process, and the accumulation of concomitants increases the tendency for constituents of the nutrient medium to precipitate, which in turn results in technical difficulties. EP A2 049 847 discloses a process for the purification of α-amylase inhibitor from culture filtrates from Streptomyces tendae by use of adsorption resins. A process for the purification of proinsulin by ®AMBERLITE XAD resins using aqueous eluents containing from 10 to 30% of acetone or acetonitrile is described in EP A2 197 764. "AMBERLITE" XAD resins are polymeric macroreticular adsorbents, commercially produced by the Rohm and Hass Company. These resins have been designed for the separation of compounds based upon varied affinities for a polymeric hydrophobic surface.

The invention has the object of developing a process with which it is possible to isolate hirudin in a straightforward manner and in good yield from complex yeast culture filtrates.

This object is achieved according to the invention by the process for the isolation and purification of hirudin from complex and salt-containing solutions by hydrophobic chromatography, which comprises carrying out the hydrophobic chromatography on porous adsorber resins with a pore diameter of 50 to 5000 Å and a specific surface area of at least 50 m$^2$/g, using as eluent a 10 to 40% strength solution of one or more organic solvents which are miscible with water.

The porous adsorber resins which are preferably used are copolymers of styrene and divinylbenzene such as, for example, "DIAION" high porous polymer (HP) 10, 20, 30, 40 or 50, or copolymers of acrylate ester and divinylbenzene such as, for example, ®AMBERLITE XAD-7 and 8 (Röhm and Haas), especially ®DIAION HP 20 and AMBERLITE XAD-7. Examples of suitable organic solvents which are miscible with water are methanol, ethanol, n-propanol, isopropanol and acetone. A solution of one organic solvent which is miscible with water is preferably used.

"DIAION" High Porous Polymers are styrene and divinylbenzene copolymers in a bead form having a macroreticular structure and manufactured by a special polymerization technique. The HP series consists of various types of HP with different surface properties. The HP series consists of HP 10, 20, 30, 40, and 50 which correspond to "AMBERLITE" XAD series. There are various types of these resins developed which have different affinities. "AMBERLITE" XAD-7 and 8 are described as follows:

a) "AMBERLITE" XAD-7 resins are unspecific absorbents consisting of acrylic acid ester. The small microbeads cluster and form a high porous structure. These resins are, in general, designed for absorption of polar compounds and are best suited for absorption of polypeptides and chromatography of phenols.

b) "AMBERLITE" XAD-8 resins are chemically identical to XAD-7, however, they form considerably larger pores. These resins are suitable for molecules of very large sizes such as proteins and nucleic acids.

The process according to the invention can be carried out in the form both of batch chromatography and of column chromatography. The resin is pre-equilibrated with an aqueous buffer or a solution of an organic acid such as, for example, 0 to 0.2 M acetic acid. The hirudin-containing solution which is applied, especially culture filtrate from Saccharomyces cerevisiae, is adjusted to a pH of 2 to 8, preferably 3 to 5, and is contacted with the resin. After the hirudin has bound completely, the resin is washed with an aqueous buffer (pH 2 to 9), for example tris or ethylenediamine, and/or a solution of an organic acid, for example 0 to 0.2 M acetic acid. The elution is then carried out with a 10 to 40 % strength solution of an organic solvent which is miscible with water. The aqueous portion of the eluent can be composed of an aqueous buffer, a solution of an organic acid such as, for example, acetic acid, or water. However, solutions of 20 to 30 % isopropanol containing 0 to 0.1 M acetic acid are preferably used in order to obtain salt-free eluates.

The process is suitable in an analogous manner for obtaining salt-free hirudin from salt-containing solutions, for example eluates from ion exchangers.

The invention is used for purifying recombinant hirudins, especially those whose expression has been brought about in Saccharomyces cerevisiae. Hirudins are to be understood to be peptide-like thrombin inhibitors which have a specific activity of at least 10,000 AT-U/mg and which are derived from the known isohirudins from the species Hirudo medicinalis and have the essential structural features thereof, especially the characteristic linkage of the three disulfide bridges (J. Dodt et al., Biol. Chem. Hoppe-Seyler 366 (1985) 379-385) (cf., for example, EP A1 158 564, EP A1 168 342, DE 3445517 A1, EP A2 193 175, EP A1 200 655, EP A1 158 986, EP A1 209 061, DE 3342139, EP A1 171 024).

They are to be understood to include especially those hirudins described in EP A1 171 024, EP A1 158 986 (corresponding to U.S. Pat. No. 4,668,662) and EP A1 209 061 (corresponding to U.S. Pat. No. 4,791,100).

U.S. Pat. No. 4,791,100 specifically discloses the amino acid sequence of the hirudin as follows:

H—(X)$_m$—A—B—C—Tyr—Thr—Asp—Cys—F—Glu—Ser—

Gly—Gln—Asn—Leu—Cys—Leu—Cys—Glu—Gly—Ser—

Asn—Val—Cys—Gly—J—Gly—Asn—Lys—Cys—Ile—Leu—

Gly—Ser—Asp—Gly—D—G—Asn—Gln—Cys—Val—Thr—

Gly—Glu—Gly—Thr—Pro—Lys—Pro—Gln—Ser—His—

Asn—Asp—Gly—Asp—Phe—Glu—E—Ile—Pro—Glu—

Glu—Tyr(R)—I—Gln—(Z)$_n$—OH

In which
m = 0–50,
n = 0–100 and
R denotes phenolic hydrogen or a phenolic ester group,
X represents identical or different radicals of naturally occurring alpha-amino acids,
Z represents identical or different radicals of naturally occurring alpha-amino acids and
A represents Ile or the absence of an amino acid,
B represents Ile or Thr or the absence of an amino acid,
C denotes Thr, Val, Ile, Leu, or Phe,
D denotes Glu or the absence of an amino acid,
E denotes Glu or Pro,
F denotes Thr or Ile,
G denotes Lys or Lys-Asp and
I denotes Ala or Leu and
J denotes Gln or Lys
in which the 6 Cys radicals are linked in pairs via disulfide bridges, and physiologically acceptable salts thereof.

The three disulfide bridges are preferably between the Cys radicals in positions 7 and 15, 17 and 29, and 23 and 40.

Naturally occurring alpha-amino acids are, in particular, Gly, Ala, Ser, Thr, Val, Leu, Ile, Asp, Asn, Glu, Gln, Cys, Met, Arg, Lys, Hyl, Orn, Cit, Tyr, Phe, Trp, His, Pro and Hyp.

R Preferably denotes hydrogen, SO$_3$H or PO$_3$H$_2$; hydrogen is particularly preferred.

Possible salts are, in particular, alkali metal and alkaline earth metal salts, salts with physiologically acceptable amines and salts with physiologically acceptable acids, such as HCl, H$_2$SO$_4$, maleic acid or acetic acid.

Preferred polypeptides of the formula I are those in which C represents Thr; and furthermore, those in which C represents Thr and A represents Ile. Particularly, suitable peptides are those where A = Ile, B = Thr, C = Thr, D = Glu, E = Glu, F = Thr, G = Lys, I = Leu, J = Gln, m = zero, n = zero and R = H or SO$_3$H;

m = zero, n = zero, R = H or SO$_3$H, A = Ile, B = direct bond,
C = Thr, D = Glu, E = Glu, F = Thr, G = Lys, I = Leu and
J = Gln;

m = zero; n = zero; R = H or So$_3$H, A = Ile, B = direct bond, C = Thr, D = Glu, E = Glu, F = Ile, G = Lys, I = Leu and J = Gln;

m = zero, n = zero, R = H or SO$_3$H, Z = Ile, B = direct bond, C = Thr, D = Glu, E = Pro, F = Thr, G = Lys, I = Leu and J = Gln;

m = zero, n = zero, R = H or SO$_3$H, A = Ile, B = direct bond, C = Thr, D = Glu, E = Pro, F = Ile, G = Lys, I = Leu and J = Gln;

m = zero, n = zero, R = H or SO$_3$H, A = direct bond, B = direct bond, C = Thr, D = direct bond, E = Glu, F = Thr, G = Lys, I = Leu and J = Gln;

A = Ile, B = direct bond, C = Thr, D = direct bond, E = Glu, F = Ile, G = Lys-Asp, I = Ala, J = Lys, m = zero, n = zero R = SO$_3$H;

A = Ile, B = direct bond, C = Thr, D = direct bond, E = Glu, F = Ile, G = Lys-Asp, I = Ala, J = Lys, m = zero, n = zero and hydrogen;

The invention also relates to the novel biologically active peptidic cleavage products which are obtained by chemical or enzymatic cleavage of these polypeptides.

The process according to the invention is distinguished by the possibility of binding hirudin quantitatively onto adsorber resin from complex and salt-containing solutions, for example complex yeast culture filtrates, without impairing the tertiary structure and activity. It is possible by elution with aqueous solutions, with the addition of organic solvents which are miscible with water, to obtain the hirudin enriched in a solution which is free of salts and substances causing turbidity and which can be directly processed further, for example by ion exchange chromatography.

The examples which follow are intended to explain the invention in detail but without restricting it to them:

EXAMPLE 1

Culture medium is taken from the fermentation of a yeast strain of the species Saccharomyces cerevisiae which corresponds to the Mat α mating type and has been transformed with yeast hirudin expression plasmid in a process analogous to that of Brake et al., PNAS, vol. 81, (1984) 4632–4646.

950 l of culture filtrate of Saccharomyces cerevisiae, containing 20 g/l yeast extract and 12 mg/l hirudin, was applied to a column of 100 l of DIAION HP 20 equilibrated with 20 mM acetic acid. Application was followed by washing with 1000 l of 50 mM tris/HCl, pH 8.5, and then 300 l of 20 mM acetic acid. Elution was then carried out with 300 l of 20 mM acetic acid containing 20% isopropanol, followed by 500 l of 20 mM acetic acid containing 30% isopropanol. The fractions of the eluate were analyzed for their hirudin content. Three fractions (150 l) were combined and contained 9.5 g of hirudin, corresponding to a yield of 84%. The acetic solution was then adjusted to pH 6.0 with 1 M piperazine and stirred with 10 kg of Matrex "CELLUFINE AM" (AMICON), which is a medium pressure DEAE ion-exchange packing for purification of low- to medium MW molecules, equilibrated with 20 mM piperazine (pH 6.0). This resulted in quantitative binding of the hirudin on the ion exchanger. The material was washed with 20 mM piperazine (pH 6.0) and packed into a column. Elution with a salt gradient from 0 to 0.3 M NaCl in the same buffer allowed 6.7 g of hirudin to be obtained highly enriched and concentrated in 6 l of solution.

EXAMPLE 2

1.2 l of an eluate from an ion exchanger, containing 2.0 g of hirudin, 20 mM piperazine (pH 6.0) and 200 mM NaCl were acidified to 0.1 M acetic acid and applied at a flow rate of 400 ml/h onto a column of 100 ml DIAION HP 20 in 0.1 M acetic acid. After the sample had been applied, the resin was washed free of salt with 10 mM acetic acid. Elution was then carried out at a flow rate of 200 ml/h with 30% isopropanol in 10 mM acetic acid. The hirudin was collected in a total volume of 200 ml. Freeze-drying of the solution resulted in 1.7 g of salt-free hirudin.

EXAMPLE 3

754 l of culture filtrate of Saccharomyces cerevisiae, containing 27.2 g of hirudin, were adjusted to pH 4 with 4.9 l of acetic acid and stirred with a suspension of 75 kg of DIAION HP 20 in 75 l of 30% strength isopropanol. After 30 minutes, the culture filtrate was removed by filtration through a pressure funnel and discarded. The adsorber resin remaining in the funnel was washed with 700 l of 20 mM tris/HCl, pH 8.5, and 250 l of 0.1 M acetic acid. The hirudin was then eluted by ten consecutive washes with 50 l of 30% isopropanol in 20 mM acetic acid each time. The eluates were analyzed for their hirudin content. Four fractions (195 l) were combined and contained 22.6 g of hirudin, corresponding to a yield of 83%.

We claim:

1. A process for isolation and purification of a hirudin from complex and salt-containing solutions by hydrophobic chromatography, which comprises carrying out the hydrophobic chromatography on porous adsorber resins selected from the group consisting of a copolymer of styrene and divinylbenzene and a copolymer of acrylate ester and divinylbenzene, using as eluent a 10 to 40% strength solution of one or more organic solvents which are miscible with water selected from the group consisting of methanol, ethanol, n-propanol, isopropanol and acetone.

2. The process as claimed in claim 1, which results in a hirudin of the formula 1:

H—(X)$_m$—A—B—C—Tyr—Thr—Asp—Cys—F—Glu—Ser—

Gly—Gln—Asn—Leu—Cys—Leu—Cys—Glu—Gly—Ser—

Asn—Val—Cys—Gly—J—Gly—Asn—Lys—Cys—Ile—Leu—

Gly—Ser—Asp—Gly—D—G—Asn—Gln—Cys—Val—Thr—

Gly—Glu—Gly—Thr—Pro—Lys—Pro—Gln—Ser—His—

Asn—Asp—Gly—Asp—Phe—Glu—E—Ile—Pro—Glu—

Glu—Tyr(R)—I—Gln—(Z)$_n$—OH

In which
  m = 0–50,
  n = 0–100 and
  R denotes phenolic hydrogen or a phenolic ester group,
  X represents identical or different radicals of naturally occurring alpha-amino acids,
  Z represents identical or different radicals of naturally occurring alpha-amino acids and
  A represents Ile or the absence of an amino acid,
  B represents Ile or Thr or the absence of an amino acid,
  C denotes Thr, Val, Ile, Leu, or Phe,
  D denotes Glu or the absence of an amino acid,
  E denotes Glu or Pro,
  F denotes Thr or Ile,
  G denotes Lys or Lys-Asp and
  I denotes Ala or Leu and
  J denotes Gln or Lys
in which the 6 Cys radicals are linked in pairs via disulfide bridges, and physiologically acceptable salts thereof.

3. The process as claimed in claim 2, which results in a hirudin of the formula I (A)$_m$—D—E—G—Tyr—L—Asp—Cys—M—Glu—Ser— (I)

Gly—Gln—Asn—Leu—Cys—Leu—Cys—Glu—Gly—Ser—

Asn—Val—Cys—Gly—N—Gly—Asn—Lys—Cys—Ile—Leu—

Gly—Ser—Asp—Q—R—T—Asn—Gln—Cys—Val—Thr—

Gly—Glu—Gly—Thr—Pro—Lys—Pro—Gln—Ser—His—

Asn—Asp—Gly—Asp—Phe—Glu—X—Ile—Pro—Glu—

Glu—Tyr(R$_1$)—Z—Gln—(A)$_n$—OH wherein
  m is 0 or 1,
  n is 0,
  A represents Val, Ile, Leu or Ala,
  D represents the absence of an amino acid,
  E represents the absence of an amino acid,
  G represents Thr or Val,
  L represents Thr,
  M represents Thr,
  N represents Gln or Lys,
  Q represents Gly,
  R represents Glu,
  T represents Lys,
  X represents Glu or Pro,
  Z represents Leu, and
  R$_1$ represents a phenolic hydrogen,
  wherein Cys 7 and Cys 15, Cys 17 and Cys 29, and Cys d23 and Cys 40 are linked in pairs via disulfide bridges,
or a physiologically acceptable salt thereof.

4. The process as claimed in claim 2, which results in the hirudin

Leu—Thr—Tyr—Thr—Asp—Cys—Thr—Glu—Ser—Gly—

Gln—Asn—Leu—Cys—Leu—Cys—Glu—Gly—Ser—Asn—

Val—Cys—Gly—Gln—Gly—Asn—Lys—Cys—Ile—Leu—

Gly—Ser—Asp—Gly—Glu—Lys—Asn—Gln—Cys—Val—

Thr—Gly—Glu—Gly—Thr—Pro—Lys—Pro—Gln—Ser—

His—Asn—Asp—Gly—Asp—Phe—Glu—Glu—Ile—Pro—

Glu—Glu—Tyr—Leu—Gln or a physiologically acceptable salt thereof.

5. The process as claimed in claim 1, wherein a copolymer of styrene and divinylbenzene is used as porous adsorber resin.

6. The process as claimed in claim 1, wherein isopropanol is used as an organic solvent.

* * * * *

UNITED STATES PATENT AND TRADEMARK OFFICE
CERTIFICATE OF CORRECTION

PATENT NO. : 5,095,092

DATED : March 10, 1992

INVENTOR(S) : Werner Badziong et al.

It is certified that error appears in the above-identified patent and that said Letters Patent is hereby corrected as shown below:

Claim 3, column 6, line 45, change "d23" to --23--.

Signed and Sealed this

Nineteenth Day of October, 1993

Attest:

BRUCE LEHMAN

Attesting Officer

Commissioner of Patents and Trademarks